United States Patent
Hwang et al.

(10) Patent No.: US 11,529,629 B2
(45) Date of Patent: Dec. 20, 2022

(54) BIOSENSOR

(71) Applicant: BBB INC., Seongnam-Si (KR)

(72) Inventors: Hyundoo Hwang, Seongnam-Si (KR); Dongsik Han, Seoul (KR); Jaekyu Choi, Seoul (KR)

(73) Assignee: BBB INC., Seongnam-si (KR)

( * ) Notice: Subject to any disclaimer, the term of this patent is extended or adjusted under 35 U.S.C. 154(b) by 85 days.

(21) Appl. No.: 15/930,073

(22) Filed: May 12, 2020

(65) Prior Publication Data
US 2020/0269244 A1 Aug. 27, 2020

Related U.S. Application Data

(63) Continuation of application No. PCT/KR2017/013252, filed on Nov. 21, 2017.

(51) Int. Cl.
*B01L 3/00* (2006.01)
*B01D 61/18* (2006.01)
*G01N 33/49* (2006.01)

(52) U.S. Cl.
CPC ........ *B01L 3/502753* (2013.01); *B01D 61/18* (2013.01); *B01L 3/502761* (2013.01); *G01N 33/491* (2013.01); *B01L 2200/0652* (2013.01); *B01L 2300/0636* (2013.01); *B01L 2300/0645* (2013.01); *B01L 2300/0681* (2013.01)

(58) Field of Classification Search
None
See application file for complete search history.

(56) References Cited

U.S. PATENT DOCUMENTS

| | | | | |
|---|---|---|---|---|
| 2001/0005488 A1* | 6/2001 | Hirao | ................... | G01N 33/491 422/535 |
| 2003/0132110 A1* | 7/2003 | Hasegawa | .............. | C12Q 1/004 204/403.02 |
| 2006/0000772 A1* | 1/2006 | Sano | .................... | B01D 71/027 210/635 |
| 2012/0329148 A1* | 12/2012 | Hur | ...................... | B01D 63/088 435/309.1 |

(Continued)

FOREIGN PATENT DOCUMENTS

| | | |
|---|---|---|
| JP | 4844318 B2 | 12/2011 |
| KR | 20130122457 A | 11/2013 |

(Continued)

*Primary Examiner* — Lore R Jarrett
(74) *Attorney, Agent, or Firm* — Studebaker & Brackett PC

(57) ABSTRACT

The present invention relates to a biosensor, including: a blood cell separation membrane which separates blood cells from blood and allows plasma components to pass through; a microfluid channel through which the plasma components that have passed through the blood cell separation membrane flow; a lower substrate which allows the plasma components that have passed through the blood cell separation membrane to flow along the microfluid channel; and a pillar which connects the blood cell separation membrane and the lower substrate, in which an electrode is disposed in the pillar, and the pillar pushes and lifts the blood cell separation membrane by a predetermined distance. The biosensor of the present invention allows plasma, which is difficult to pass through the blood cell separation membrane due to surface tension, to easily pass through.

12 Claims, 5 Drawing Sheets

(56) References Cited

U.S. PATENT DOCUMENTS

2014/0367317 A1\* 12/2014 Neijzen .................. B01L 3/502
                                                                                          210/95
2020/0095527 A1\* 3/2020 Oba ....................... C12M 25/02

FOREIGN PATENT DOCUMENTS

| KR | 20150009745 A | 1/2015 |
| KR | 20160129937 A | 11/2016 |

\* cited by examiner

BIOSENSOR

CROSS-REFERENCE TO RELATED APPLICATIONS

The present application is a continuation of International Patent Application No. PCT/KR2017/013252 filed on Nov. 21, 2017. The disclosures of the above-listed applications are hereby incorporated by reference herein in their entirety.

TECHNICAL FIELD

The present invention relates to a biosensor, and more particularly, to a biosensor capable of allowing plasma, which is difficult to pass through a blood cell separation membrane due to surface tension, to easily pass through.

BACKGROUND ART

FIGS. 1A to 1B are diagrams of a biosensor in the related art.

Referring to FIGS. 1A to 1B, the biosensor in the related art includes a blood cell separation membrane 100, a microfluid channel 110, a lower substrate 120, and a spacer 130. FIG. 1A is a diagram of a biosensor viewed from the top, and FIG. 1B is a cross-sectional view of the biosensor taken along line A-A'.

Blood cells contained in blood are filtered by the blood cell separation membrane 100, and when plasma components pass through the blood cell separation membrane 100, the passing plasma components flow through the microfluid channel 110.

The general blood cell separation membrane 100 is formed with holes having a smaller size than that of the blood cell, and when the blood cell separation membrane 100 absorbs the blood cell and the plasma, there is a problem in that the plasma does not escape from the blood cell separation membrane 100 due to surface tension.

In this case, in the related art, a method of moving the plasma components to another region by a capillary phenomenon by applying pressure from the outside or bonding another membrane is used. Accordingly, it is necessary to more effectively lower surface tension so that the plasma easily passes through the blood cell separation membrane.

DISCLOSURE

Technical Problem

Accordingly, a technical problem to be solved by the present invention is to provide a biosensor capable of allowing plasma, which is difficult to pass through a blood cell separation membrane due to surface tension, to easily pass through.

Another technical problem to be solved by the present invention is to provide an apparatus for measuring blood sugar capable of directly measuring plasma that has passed through a blood cell separation membrane through an electrode disposed in a pillar by locating a hydrophilically treated pillar between the blood cell separation membrane and a lower substrate and disposing the electrode in the pillar.

Technical Solution

In order to achieve the object, the present invention provides a biosensor, including: a blood cell separation membrane which separates blood cells from blood and allows plasma components to pass through; a microfluid channel through which the plasma components that have passed through the blood cell separation membrane flow; a lower substrate which allows the plasma components that have passed through the blood cell separation membrane to flow along the microfluid channel; and a pillar which connects the blood cell separation membrane and the lower substrate, in which an electrode is disposed in the pillar, and the pillar pushes and lifts the blood cell separation membrane by a predetermined distance.

According to an exemplary embodiment of the present invention, an electrode may be disposed in the pillar, and a portion of the pillar that is in contact with the blood cell separation membrane may be formed of an insulator.

Further, the electrode may be formed in a lateral portion of the pillar.

Further, the pillar may have an inner empty space to allow the plasma components that have passed through the blood cell separation membrane to flow along the empty space.

According to another exemplary embodiment of the present invention, surface tension may be lowered by applying piezoelectric or ultrasonic vibration to the pillar. In this case, the pillar may have a porous structure, and a surface of the pillar may be hydrophilic.

In order to achieve the object, the present invention provides a biosensor, including: a blood cell separation membrane which separates blood cells from blood and allows plasma components to pass through; a lower substrate in which plasma components that have passed through the blood cell separation membrane are stored; and a plurality of pillars which connects the blood cell separation membrane and the lower substrate, in which the plurality of pillars is located at a border of a space formed between the blood cell separation membrane and the lower substrate at a predetermined interval, and an electrode is disposed in at least one of the plurality of pillars.

In this case, a space between the plurality of pillars may be filled with hydrogel.

In order to achieve the object, the present invention provides a device for measuring blood sugar, the device including: a blood cell separation membrane which separates blood cells from blood and allows plasma components to pass through; a microfluid channel through which the plasma components that have passed through the blood cell separation membrane flow; a lower substrate which allows the plasma components that have passed through the blood cell separation membrane to flow along the microfluid channel; and a pillar which connects the blood cell separation membrane and the lower substrate, and pushes and lifts the blood cell separation membrane by a predetermined distance; an electrode disposed in the pillar; a housing which has an inner accommodation space and is formed with an insertion port, to which the electrode is insertable, at one side; two or more contact pins which are disposed in the inner space of the housing and are in contact with the electrode; and a signal processing unit which measures and analyzes a current amount transmitted through the electrode and converts blood sugar to a numerical value.

According to an exemplary embodiment of the present invention, the device may further include a plasma saturation determining unit which performs a measurement of blood sugar by using the device for measuring blood sugar at least three times, and determines that the plasma is collected between the electrodes and is saturated when a change of a measured blood sugar value is within a predetermined range.

Advantageous Effects

According to the present invention, it is possible to allow plasma, which is difficult to pass through a blood cell separation membrane due to surface tension, to easily pass through. Further, according to the present invention, a hydrophilically treated pillar is located between a blood cell separation membrane and a lower substrate and an electrode is disposed in the pillar, so that it is possible to immediately measure plasma that has passed through the blood cell separation membrane through the electrode disposed in the pillar.

DETAILED DESCRIPTION

Figure 1A:
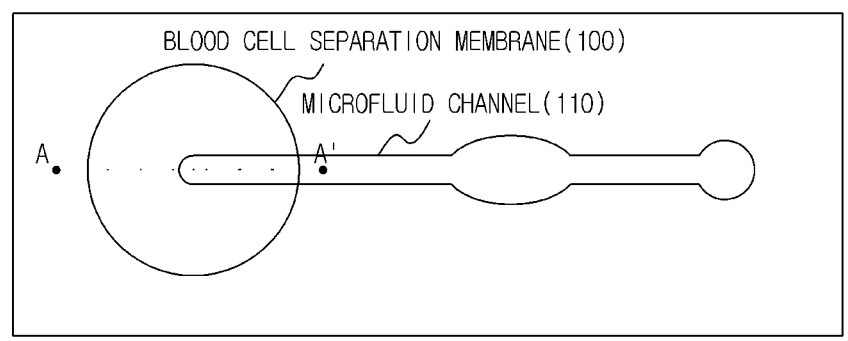
FIGS. 1A to 1B are diagrams of a biosensor in the related art.
Figure 1B:
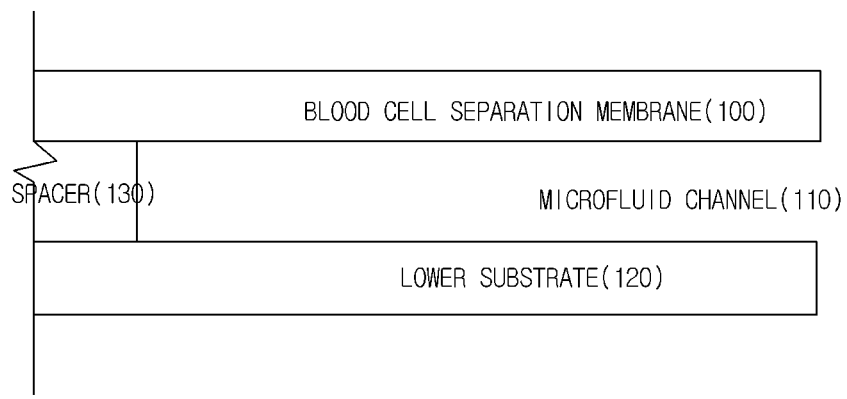

In order to achieve the object, the present invention provides a biosensor, including: a blood cell separation membrane which separates blood cells from blood and allows plasma components to pass through; a microfluid channel through which the plasma components that have passed through the blood cell separation membrane flow; a lower substrate which allows the plasma components that have passed through the blood cell separation membrane to flow along the microfluid channel; and a pillar which connects the blood cell separation membrane and the lower substrate, in which an electrode is disposed in the pillar, and the pillar pushes and lifts the blood cell separation membrane by a predetermined distance.

Hereinafter, in order to describe the present invention in more detail, exemplary embodiments of the present invention will be described in more detail with reference to the accompanying drawings. However, the present invention is not limited to the exemplary embodiment described herein, and may also be specified in another form. In the drawings, when it is said that a layer is formed "on" another layer or a substrate, the layer may be directly formed on another layer or the substrate, or may be formed on the another layer or the substrate with a third layer interposed therebetween.

It will be understood that when an element or a layer is referred to as being "on" another element or layer, it can be directly on another element or layer or an intervening layer or element may also be present. In contrast, when an element is referred to as being "directly on" another element, there are no intervening element or layer present. The spatially relative terms, "below, "beneath", "lower", "above", "upper", and the like may be used for easily describing the correlation of one element or constituent component with another element or constituent components as illustrated in the drawings. The spatially relative terms should be understood as the terms including different directions of the elements when the elements are used or operated in addition to the direction illustrated in the drawing. For example, when an element illustrated in the drawing is turned over, the element described as being "below or beneath" the other element may be placed "above" the other element. Accordingly, the illustrative term "below or beneath" may include both the directions below and above. The element may also be oriented in a different direction, and in this case, the spatially relative terms may be interpreted according to the orientation.

The present invention may have various modifications and exemplary embodiments and thus specific exemplary embodiments will be illustrated in the drawings and described. However, it is not intended to limit the present invention to the specific exemplary embodiments, and it will be appreciated that the present invention includes all modifications, equivalences, or substitutions included in the spirit and the technical scope of the present invention.

Figure 2A:
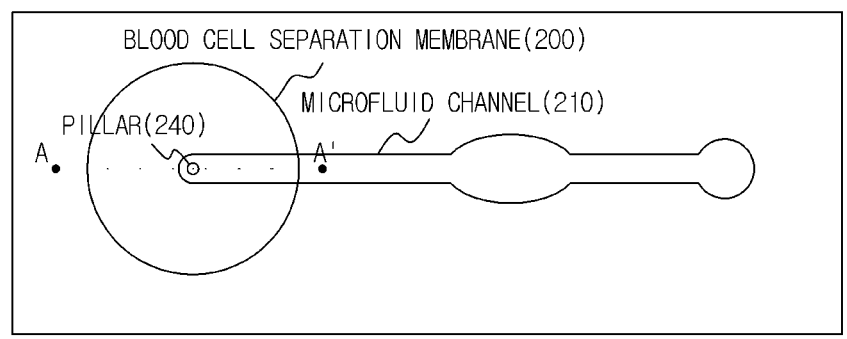
FIGS. 2A to 2B are diagrams illustrating a biosensor according to an exemplary embodiment of the present invention.
Figure 2B:
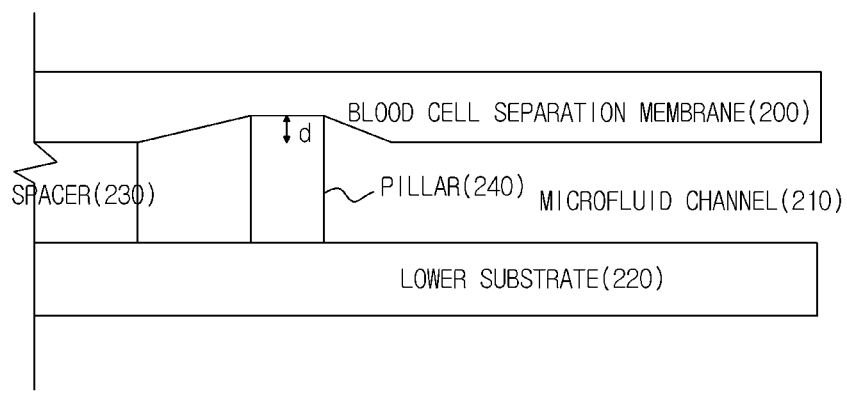

FIGS. 2A to 2B are diagrams illustrating a biosensor according to an exemplary embodiment of the present invention.

Referring to FIGS. 2A to 2B, the biosensor according to the exemplary embodiment of the present invention includes a blood cell separation membrane 200, a microfluid channel 210, a lower substrate 220, a spacer 230, and a pillar 240. FIG. 2A is a diagram of a biosensor viewed from the top, and FIG. 2B is a cross-sectional view of the biosensor taken along line A-A'.

The blood cell separation membrane 200 separates blood cells and plasma while components with difference sizes in the blood move in the direction of gravity. The blood cells are caught and separated in pores constituting the blood cell separation membrane 200, and the plasma components pass through the blood cell separation membrane 200. A material of the blood cell separation membrane may be polysulfone. In the present specification, the plasma component is meant to include plasma and serum.

Before receiving the blood to be tested, plasma priming may be supplied to a lower surface of the blood cell separation membrane 200 to lower surface tension. As the plasma priming, it is preferable to use a solution composed of sodium, magnesium, and potassium levels similar to that of the plasma.

The microfluid channel 210 is a passage through which the plasma components that have passed through the blood cell separation membrane 200 flow. A flow speed of the plasma component may be changed by one or more of a length, a width, and a volume of the microfluid channel 210.

The lower substrate 220 allows the plasma components that have passed through the blood cell separation membrane 200 to flow along the microfluid channel 210. The lower substrate 220 may be hydrophilic.

The spacer 230 is located between the lower substrate 220 and the blood cell separation membrane 200, and spaces the lower substrate 220 and the blood cell separation membrane 200.

The pillar 240 connects the blood cell separation membrane 200 and the lower substrate 220. In this case, the pillar 240 may push and lift the blood cell separation membrane 200 by a predetermined distance d.

In the case where the electrode is disposed in the pillar 240, when the plasma components are collected between the blood cell separation membrane 200 and the lower substrate 220, the plasma components are easily in contact with the electrode, thereby more easily analyzing the plasma components.

In the meantime, a surface in which the pillar 240 is in contact with the blood cell separation membrane 200, may be formed of an insulator, and the pillar 240 may have a porous structure.

Further, an empty space is provided inside the pillar 240, and the plasma components that have passed through the blood cell separation membrane 200 may flow along the empty space.

The surface of the pillar 240 may be hydrophilically treated in order to reduce surface tension, and piezoelectric vibration or ultrasonic vibration of the natural frequency of the pillar may be applied to the pillar 240.

Further, the pillar 240 itself may be formed of a hydrophilic material, or the surface of the pillar may be hydrophilic. As one exemplary embodiment, the hydrophilic material of the pillar 240 may be hydrogel.

Figure 3A:
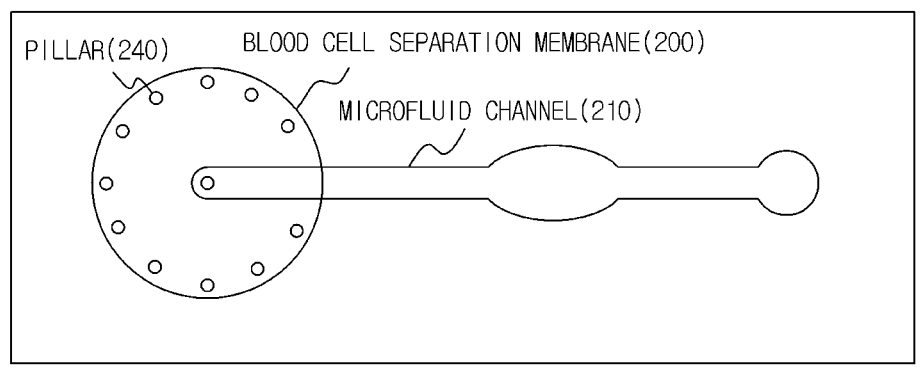
FIGS. 3A to 3C are diagrams illustrating a biosensor according to another exemplary embodiment of the present invention.
Figure 3B:
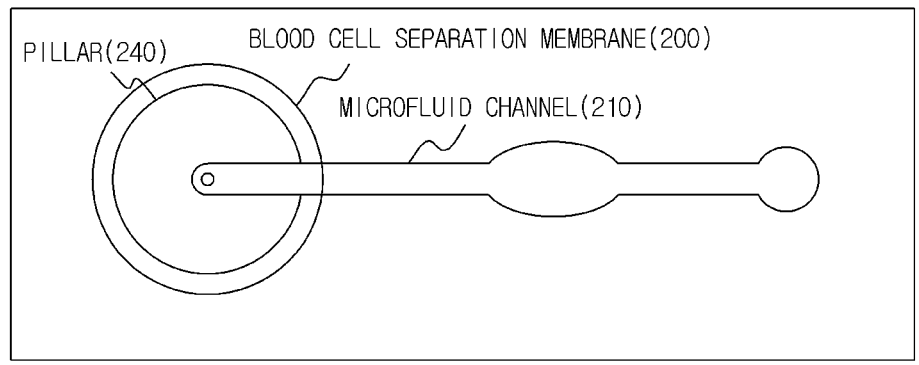
Figure 3C:
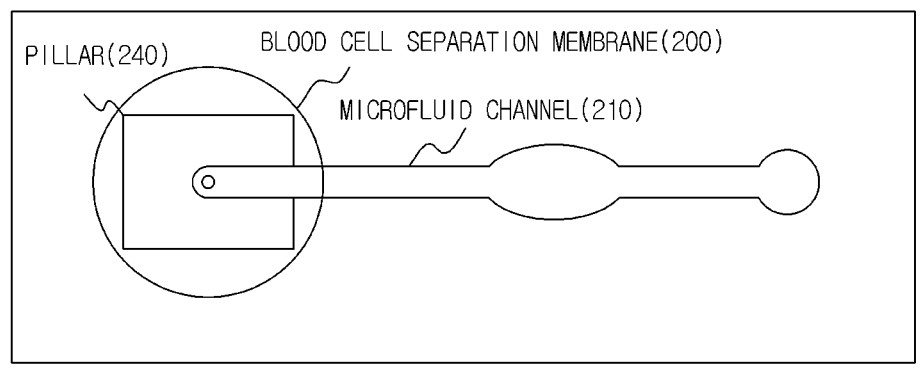

FIGS. 3A to 3C are diagrams illustrating a biosensor according to another exemplary embodiment of the present invention.

FIG. 3A illustrates the case where pillars 240 are located along a border of a space formed between a blood cell separation membrane 200 and a lower substrate 220 at a predetermined interval. In FIG. 2A, the number of pillars is one in the center of the blood cell separation membranes 200, but in FIG. 3A, and the pillars 240 are located along the border of the space formed between the blood cell separation membrane 200 and the lower substrate 220 at the predetermined interval, so that plasma components that have passed through the blood cell separation membrane 200 cannot pass between the pillars due to surface tension. As a result, there is an effect in that the plasma components are collected inside the pillar.

In this case, electrodes may be disposed in the plurality of pillars located in the circumference of the blood cell separation membrane 200 to analyze the plasma components collected inside the pillars.

As the exemplary embodiment in which the electrodes are disposed in the plurality of pillars, lateral portions of the plurality of pillars may be formed with the electrodes.

Further, the space between the blood cell separation membrane 200 and the lower substrate 220 may be filled with hydrogel. Accordingly, the space between the plurality of pillars is filled with hydrogel.

FIG. 3B illustrates the case where one surface of a pillar 240 is in contact with a circumference of a blood cell separation membrane 200 and a lower substrate 220, and the pillar 240 has a cylindrical structure having an empty inner space. In this case, an electrode may be disposed in an inner lateral surface of the cylindrical structure.

FIG. 3C illustrates the case where one surface of a pillar 240 is in contact with a circumference of a blood cell separation membrane 200 and a lower substrate 220, and the pillar 240 has a square pillar having an empty inner space. In this case, an electrode may be disposed in an inner lateral surface of the square pillar structure.

A discharge port, through which the filled plasma components are discharged, may be further provided inside the pillar having the cylindrical structure of the square pillar structure illustrated in FIG. 3B and FIG. 3C.

Figure 4A:
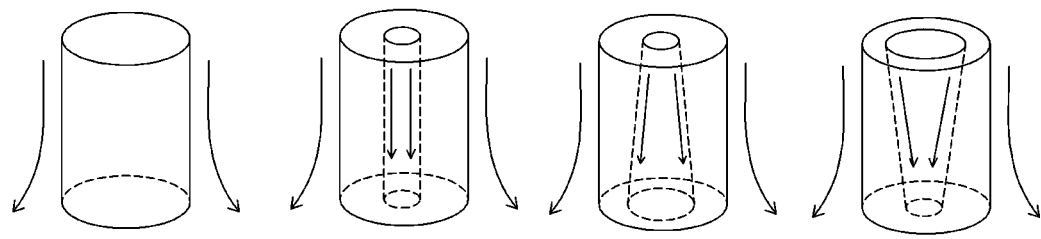
FIGS. 4A to 4C are diagrams illustrating various structures of pillars illustrated in FIGS. 2A to 2B and FIG. 3A.
Figure 4B:
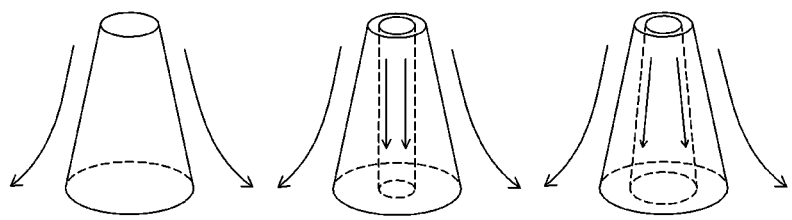
Figure 4C:
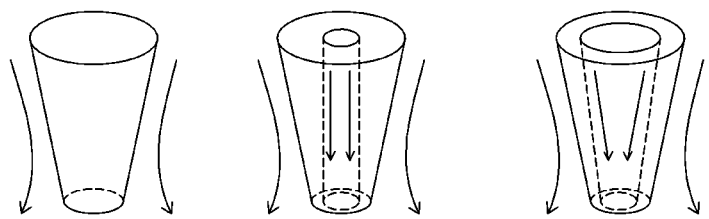

FIGS. 4A to 4C are diagrams illustrating various structures of the pillars illustrated in FIGS. 2A to 2B and FIG. 3A.

FIG. 4A illustrates various exemplary embodiments of the case where the pillar 240 is a cylindrical pillar.

Referring to FIG. 4A, there is a case where the plasma components that have passed through the blood cell separation membrane 200 descend on an outer wall of the pillar of the cylindrical pillar. Further, in the case where there is a cylindrical space, a conical column shaped space with a narrower upper end than a lower end, or an inverted conical column shaped space with a wider upper end than a lower end is provided inside the pillar, the plasma components may descend on an inner wall, as well as the outer wall of the pillar, by gravity.

FIG. 4B illustrates various exemplary embodiments of the case where the pillar 240 is shaped like the conical column with the narrower upper end than the lower end.

Referring to FIG. 4B, there is a case where the plasma components that have passed through the blood cell separation membrane 200 descend on an outer wall of the pillar shaped like the conical column with the narrower upper end than the lower end. Further, in the case where the cylindrical space or the space shaped like the conical column with the narrower upper end than the lower end is provided inside the pillar, the plasma components may descend on an inner wall, as well as the outer wall of the pillar, by gravity.

FIG. 4C illustrates various exemplary embodiments of the case where the pillar 240 is shaped like the inverted conical column with the wider upper end than the lower end.

Referring FIG. 4C, there is a case where the plasma components that have passed through the blood cell separation membrane 200 descend on an outer wall of the pillar shaped like the inverted conical column with the wider upper end than the lower end. Further, in the case where the cylindrical space or the space shaped like the inverted conical column with the wider upper end than the lower end is provided inside the pillar, the plasma components may descend on an inner wall, as well as the outer wall of the pillar, by gravity.

When plasma is applied to the electrode included in the biosensor according to the exemplary embodiment of the present invention and power is applied, the predetermined amount of current is generated in the electrode. In this case, the generated amount of current is in proportion to a concentration of glucose in the blood, so that it is possible to measure the concentration of glucose in the blood by calculating a mean value or a median of the amount of current.

Figure 5:
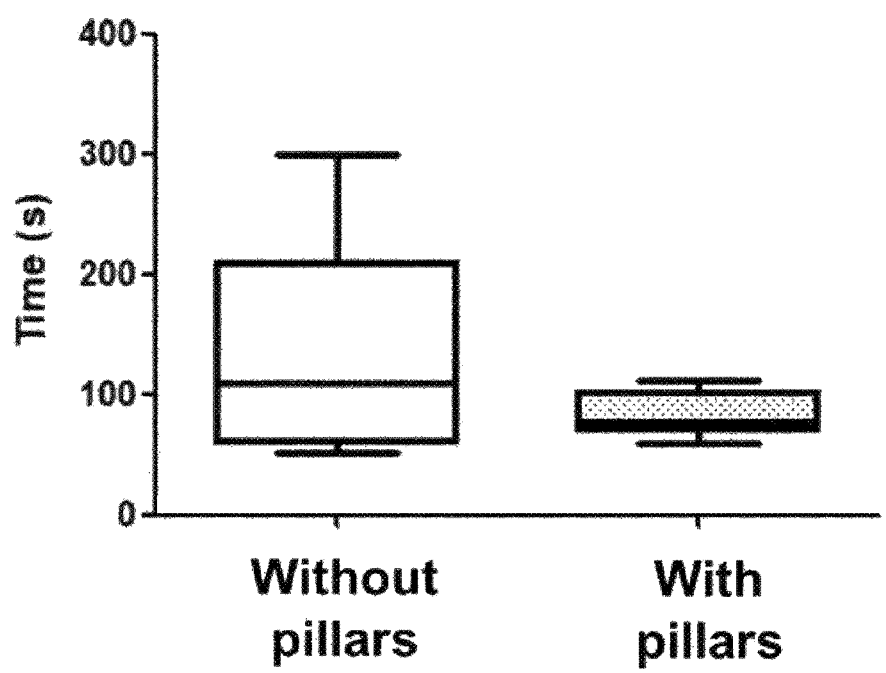
FIG. 5 is a graph illustrating a comparison of a plasma discharge time between the biosensor including the pillar according to the exemplary embodiment of the present invention and a biosensor having no pillar.

FIG. 5 is a graph illustrating a comparison of a plasma discharge time between the biosensor including the pillar according to the exemplary embodiment of the present invention and a biosensor having no pillar.

Since a rate at which the plasma passes through the blood cell separation membrane from whole blood changes according to the amount of whole blood that has not yet passed, the rate is not linearly changed. Accordingly, the graph in the candle form of FIG. 5 is used for description.

A y-axis of FIG. 5 represents the time taken to discharge 4 μL (microliters) of plasma when 40 μL of whole blood is injected.

A horizontal bar at the top of the box means the time taken for 99% of the plasma to escape, an upper end of the box means the time taken for 75% of the plasma to escape, a lower end of the box means the time taken for 25% of the plasma to escape, a horizontal bar at the bottom of the box means the time taken for 1% of the plasma to escape, and a horizontal bar within the box means an average time.

Referring to FIG. 5, when the rate at which the plasma escapes in the case where the pillar is included is compared with the rate at which the plasma escapes in the case where the pillar is not included, the time taken for 99% of the plasma to escape in the case where the pillar is included is about 100 s, and the time taken for 99% of the plasma to escape in the case where the pillar is not included is about 300 s, so that it can be seen that the time is decreased by ⅓.

The biosensor according to the exemplary embodiment of the present invention is applicable to a measuring device for other micro samples, such as lactose or cholesterol, as well as a blood sugar measuring device.

A device for measuring blood sugar according to an exemplary embodiment of the present invention includes: a blood cell separation membrane which separates blood cells from blood and allows plasma components to pass through, a microfluid channel through which the plasma components that have been passed through the blood cell separation membrane flow, a lower substrate which allows the plasma components that have been passed through the blood cell separation membrane to flow along the microfluid channel, a pillar which connects the blood cell separation membrane and the lower substrate and pushes and lifts the blood cell separation membrane by a predetermined distance, an electrode disposed in the pillar, a housing which has an inner accommodation space and is formed with an insertion port, to which the electrode is insertable, at one side, two or more contact pins which are disposed in the inner space of the housing and are in contact with the electrode, and a signal processing unit which measures and analyzes the amount of current transmitted through the electrode and converts sugar blood to a numerical value.

Further, the device for measuring blood sugar may further include a plasma saturation determining unit which performs a measurement of blood sugar by using the device for measuring blood sugar at least three times, and determines that the plasma is collected between the electrodes and is saturated when a change of the measured blood sugar value is within a predetermined range.

As described above, the present invention has been described by the specific matters, such as a specific component, limited embodiments, and drawings, but these are provided only for helping general understanding of the present invention, and the present invention is not limited to the exemplary embodiments, and those skilled in the art will appreciate that various modifications, additions and substitutions are possible from the invention.

The spirit of the present invention is defined by the appended claims rather than by the description preceding them, and all changes and modifications that fall within metes and bounds of the claims, or equivalents of such metes and bounds are therefore intended to be embraced by the range of the spirit of the present invention.

The invention claimed is:

1. A biosensor, comprising:
a blood cell separation membrane comprising pores to separate blood cells from blood and to allow plasma components to pass through the membrane;
a microfluid channel through which the plasma components that have passed through the blood cell separation membrane flow;
a lower substrate which allows the plasma components that have passed through the blood cell separation membrane to flow along the microfluid channel;
a spacer positioned between the lower substrate and the blood cell separation membrane; and
a pillar which connects the blood cell separation membrane and the lower substrate,
wherein an electrode is disposed in the pillar, and the pillar is positioned on a top surface of the lower substrate, and
wherein the pillar is configured to support the blood cell separation membrane, such that a portion of a bottom surface of the blood cell separation membrane supported by the pillar is lifted higher than a top surface of the spacer.

2. The biosensor of claim 1, wherein the electrode is formed in a lateral portion of the pillar.

3. The biosensor of claim 1, wherein a portion of the pillar that is in contact with the blood cell separation membrane is formed of an insulator.

4. The biosensor of claim 1, wherein the pillar has an inner empty space to allow the plasma components that have passed through the blood cell separation membrane to flow along the empty space.

5. The biosensor of claim 1, wherein a surface of the pillar is hydrophilic.

6. The biosensor of claim 1, wherein the pillar has a porous structure.

7. The biosensor of claim 1, wherein the blood cell separation membrane has a disk shape, and
wherein the pillar has a cylinder shape and is positioned under a center portion of the blood cell separation membrane.

8. A biosensor, comprising:
a blood cell separation membrane comprising pores to separate blood cells from blood and to allow plasma components to pass through the membrane;
a lower substrate in which plasma components that have passed through the blood cell separation membrane are stored;
a spacer positioned between the lower substrate and the blood cell separation membrane;
a plurality of pillars located at a border of a space formed between the blood cell separation membrane and the lower substrate;
an electrode disposed in at least one of the plurality of pillars,
wherein the plurality of pillars are separated from each other, and
wherein each of the plurality of pillars is positioned on a top surface of the lower substrate and is configured to support the blood cell separation membrane, such that a plurality of portions of a bottom surface of the blood cell separation membrane supported by the plurality of pillars are lifted higher than a top surface of the spacer.

9. The biosensor of claim 8, wherein a space between the plurality of pillars is filled with hydrogel.

10. The biosensor of claim 8, wherein the blood cell separation membrane has a disk shape, and
wherein the plurality of pillars are disposed along a circumference of the blood cell separation membrane.

11. A device for measuring blood sugar, the device comprising:
a blood cell separation membrane comprising pores to separate blood cells from blood and to allow plasma components to pass through the membrane;
a microfluid channel through which the plasma components that have passed through the blood cell separation membrane flow;
a lower substrate which allows the plasma components that have passed through the blood cell separation membrane to flow along the microfluid channel;
a spacer positioned between the lower substrate and the blood cell separation membrane; and
a pillar which connects the blood cell separation membrane and the lower substrate, wherein the pillar is positioned on a top surface of the lower substrate and is configured to support the blood cell separation membrane, such that a portion of a bottom surface of the blood cell separation membrane supported by the pillar is lifted higher than a top surface of the spacer;

an electrode disposed in the pillar;

a housing which has an inner accommodation space and is formed with an insertion port, to which the electrode is insertable, at one side; and two or more contact pins which are disposed in the inner space of the housing and are in contact with the electrode.

12. The device of claim 11, wherein the blood cell separation membrane has a disk shape, and wherein the pillar has a cylinder shape and is positioned under a center portion of the blood cell separation membrane.

\* \* \* \* \*